(12) United States Patent
Berson et al.

(10) Patent No.: US 6,720,178 B1
(45) Date of Patent: Apr. 13, 2004

(54) SELF-FEEDING ROLLER BOTTLE

(75) Inventors: Robert E. Berson, Louisville, KY (US); Goetz Friederichs, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 256 days.

(21) Appl. No.: 09/896,819

(22) Filed: Jun. 29, 2001

Related U.S. Application Data
(60) Provisional application No. 60/215,385, filed on Jun. 29, 2000.

(51) Int. Cl.[7] .............................................. C12M 1/10
(52) U.S. Cl. ............................. 435/298.2; 435/294.1; 435/304.2; 366/235
(58) Field of Search .................... 435/288.1, 288.2, 435/293.1, 293.2, 294.1, 298.2, 299.2, 304.1–304.3; 366/235

(56) References Cited

U.S. PATENT DOCUMENTS

| | | | |
|---|---|---|---|
| 2,686,754 A | * | 8/1954 | Monod ..................... 435/298.2 |
| RE24,822 E | * | 5/1960 | Pallotta et al. ......... 210/321.68 |
| 3,939,237 A | | 2/1976 | Naito et al. ..................... 264/54 |
| 4,184,916 A | | 1/1980 | Tolbert et al. ............... 435/241 |
| 4,310,630 A | | 1/1982 | Girard et al. ............... 435/284 |
| 4,342,904 A | | 8/1982 | Onsager ..................... 235/493 |
| 4,537,860 A | | 8/1985 | Tolbert et al. ............... 435/240 |
| 4,740,104 A | | 4/1988 | Stohr et al. ..................... 405/36 |
| 4,897,356 A | * | 1/1990 | Simpson et al. ............. 435/262 |
| 4,962,033 A | | 10/1990 | Serkes et al. ......... 435/240.243 |
| 4,988,623 A | | 1/1991 | Schwartz et al. ........... 435/286 |
| 5,057,428 A | | 10/1991 | Mixutani et al. ........... 435/285 |
| 5,556,765 A | | 9/1996 | Dedolph ....................... 435/41 |
| 5,637,224 A | | 6/1997 | Sirkar et al. ................ 210/644 |
| 5,672,507 A | | 9/1997 | Merk ....................... 435/295.2 |
| 5,705,350 A | | 1/1998 | Mudryj et al. ............. 435/7.21 |
| 5,705,390 A | | 1/1998 | Kadouri et al. ............. 435/395 |
| 5,924,583 A | | 7/1999 | Stevens et al. ................ 215/40 |
| 5,945,338 A | | 8/1999 | Spaulding et al. .......... 435/394 |
| 5,958,763 A | | 9/1999 | Goffe ....................... 435/303.1 |
| 6,001,642 A | | 12/1999 | Tsao ........................ 435/297.3 |
| 6,001,643 A | * | 12/1999 | Spaulding ................ 435/298.2 |

* cited by examiner

*Primary Examiner*—William H. Beisner
(74) *Attorney, Agent, or Firm*—Schwegman, Lundberg, Woessner & Kluth, P.A.

(57) ABSTRACT

A reservoir is provided with a spiroid pump which enables the automatic transfer of fresh medium into a roller bottle culture chamber. The reservoir may be formed from a portion of a culture chamber or may be a separate bottle.

2 Claims, 3 Drawing Sheets

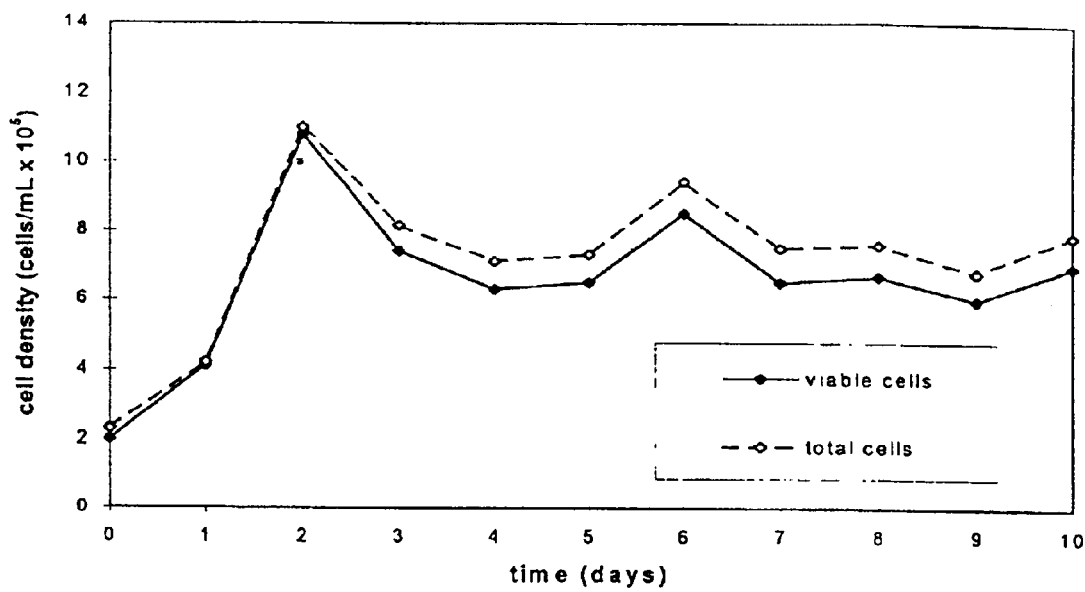
FIGURE 2. AE-1 Cell Culture in the Spi-Roll Bottle, 50% dilution.
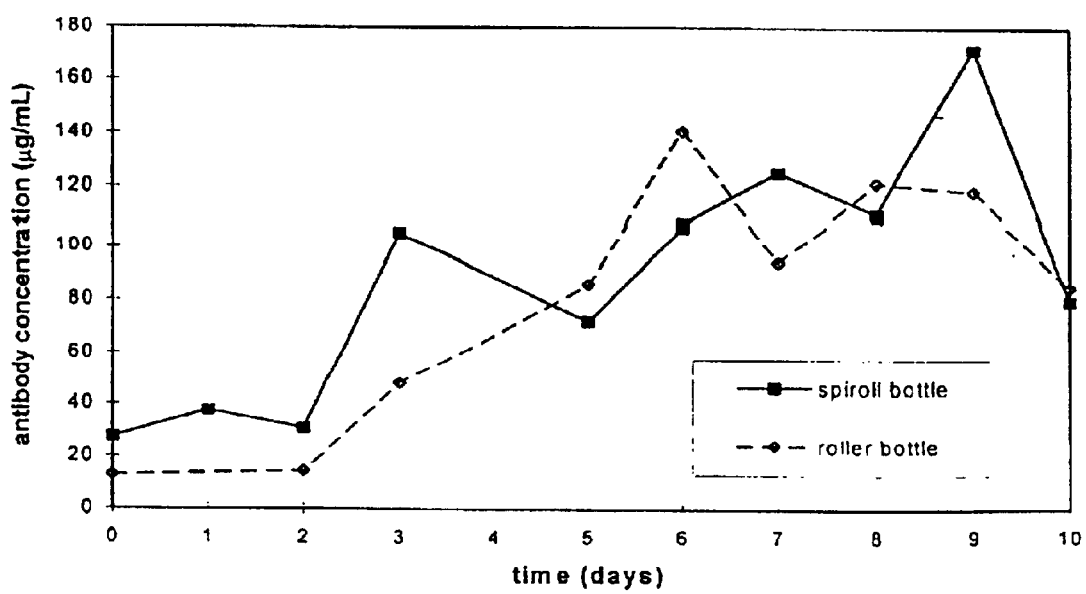
FIGURE 3. Antibody Production in the Spi-Roll and Roller Bottles, 37.5% dilution.

SELF-FEEDING ROLLER BOTTLE

RELATED APPLICATION

This application claims benefit of U.S. Provisional Application Ser. No. 60/215,385, filed Jun. 29, 2000.

BACKGROUND OF THE INVENTION

For millennia, various types of cells have been known to be useful to manufacture products. Among these cells are bacteria, yeast, plant, insect and mammalian cells. For example, beer and wine were made with the use of yeast cells by the ancient Egyptians. Many of the useful cells have robust physiology and structure and can be grown successfully as suspension cultures in stationary vats. If it is necessary to mix the culture in order to provide air or nutrients, paddles and/or air lifts can be used. However, these methods of mixing and aeration cause shearing and destruction of more delicate cells such as insect and mammalian cells, and bacterial, plant and yeast protoplasts. Such suspension cultures are not useful for cells that require attachment to a substrate for growth.

Roller bottles, in which the culture is mixed by the rotation of culture bottles on a roller, have long been used to bathe cells gently in nutrient and to expose them to air. Roller bottles also provide a surface for cells that require a substrate on which to attach.

However, a serious drawback to roller bottles is that in order to add fresh culture medium or to withdraw spent medium, it is necessary to open the bottles or to add/withdraw fluid by syringe, time-consuming and labor intensive tasks, which increase the possibility of contamination.

Roller bottle cell culture is well known. A roller table of any desirable size is equipped with a series of rollers. When these rollers are driven by a motor to rotate, bottles placed within the declivity between two rollers will rotate, providing gentle mixing of the bottle contents. Mixing is improved in some models by molding baffles on the inside surface of the bottle or providing paddles.

Comparison of monascus pigments produced by the fungus Monascus anka show the advantages of mixed versus stationary cultures. Cells were grown in batch-submerged, agar surface and roller bottle culture. The cells grown in the roller bottle produced a pigment yield about ten times greater than that of the other two systems. The time required for maximum pigment production was four days in the roller bottle compared to seven days for the batch-submerged and agar cultures.

The addition of nutrient also improves product yield. With hybridomas grown in a typical batch culture, the number of viable cells varies with time. A batch culture begins with a lag phase, where there is no increase in cell number. Following the lag phase, a period of exponential growth occurs in the logarithmic phase. A stationary phase follows where the cell population is at a maximum size. Finally, a decline in cell number occurs in the death phase. Reuveny et al investigated monoclonal antibody production in four different systems using a single hybridoma cell line. The four systems employed were fed-batch, semi-continuous, two-stage semi-continuous and perfusion. Each was compared to batch culture.

In the fed-batch system, a spinner flask was initially inoculated with 60 milliliters of culture media. When the cell density reached a value just below its known peak in batch mode, daily addition of six milliliters of fresh media was added to the culture. This method maintained the viable cell concentration between five and eight times the level found in batch cultures. The amount of antibody present on day eight was almost double that found in the batch system while the total media used was approximately equal. This fed-batch method of propagation resulted in an average antibody production rate of 27 micrograms per milliliter per day, as compared to a daily average production rate of 15 micrograms per milliliter per day in the batch control.

The semi-continuous system employed a system in which 100 milliliter cultures in spinner flasks were fed twice daily. Each day prior to the first feeding, a volume equivalent to the amount of media to be fed that day was removed. Fresh media was then added every 12 hours. Four tests were run where media volumes ranging from five percent to 40 percent of the total culture volume was replaced daily. The replacement rate of 20 percent resulted in the highest average daily antibody production rate equal to 34 milligrams per milliliter per day. The two-stage semi-continuous system involved a semi-continuous feeding strategy as above, but, instead of harvesting antibody from the cultures that were removed daily, a second stage vessel was used to feed the removed culture in order to maintain cell viability. With this second stage, a productivity rate of 62 micrograms per milliliter per day was obtained.

The perfusion culture system was constructed by mounting a cylindrical filter with five micrometer openings around the stirring shaft of a one liter reactor. Since the hybridomas are larger than ten micrometers, the screen retains the cells and allows cell-free supernatant to collect in the inner part of the rotating cylinder. Continuous perfusion occurred by controlled addition of fresh media to the culture on the outside of the cylinder while pumping out cell-free supernatant from within the cylinder at the same rate. Perfusion was initiated when cells reached their maximum density in batch. The feeding was initiated at a rate of 27 percent of total reactor volume per day. The rate had to be increased daily until the cell density leveled off at a maximum value. The feeding rate reached 1790 percent of the reactor volume per day (1,700 milliliters per day in the one liter reactor). Antibody production was high, averaging 660 micrograms per milliliter per day.

Many other attempts have succeeded in devising systems that maintain viability and production. In general, these systems have either been complex and expensive in initial apparatus cost and or simple but very labor-intensive.

The need remains to attain a high level of cell growth and/or production, simply, without cumbersome and expensive equipment or high labor input.

SUMMARY OF THE INVENTION

This invention provides a reservoir chamber having a spiroidal pump formed of tubing placed in a spiral on the inside surface of the reservoir chamber. The inlet end of the tubing is open to the reservoir while the outlet end is open to a growth chamber. The reservoir chamber is attached to the growth chamber so that the two chambers rotate synchronously on their horizontal axes when placed on a moving roller table. The reservoir chamber and growth chamber may be formed by dividing a roller bottle with an partition that is impermeable to fluids. Alternatively, the reservoir chamber may be a separate bottle attached to the growth chamber. Each bottle is fitted with a removable cap, which is preferably a filter of such a mesh as to allow the passage of fluids but not particles such as bacteria. The growth chamber is partially filled with inoculated culture medium, while the reservoir chamber is partially filled with replacement medium. Upon rotation, the inlet end of the tubing will fill first with replacement medium and then with air as the chamber is rotated. The "plugs" of air and medium move along the tubing with continued rotation and empty into the growth chamber. The volumetric feeding rate at which fresh replacement medium is moved from the reservoir chamber to the roller bottle can be varied by varying the diameter of the tubing and/or the rotation rate.

Also provided is a collection bottle, attached to the growth chamber distal to the attachment of the reservoir chamber, so that when the culture medium in the growth chamber reaches a predetermined level, the medium will overflow into the collection bottle. Preferably, the collection bottle is fitted with a valve and connect/disconnect fitting so that it can be removed and replaced with another collection bottle. If the reservoir chamber is a bottle separate from the growth chamber, it is advantageous to fit the reservoir chamber also with a valve and connect/disconnect fitting. Thus this invention provides a means of feeding and harvesting the contents of the system quickly and conveniently without opening the growth chamber.

DESCRIPTION OF THE DRAWINGS

FIG. 2 shows AE-1 cell culture grown in the test bottle.

FIG. 3 shows antibody production in the test bottle as compared to batch-fed conventional bottle.

DETAILED DESCRIPTION OF THE INVENTION

The invention will now be described in terms of specific embodiments. Each embodiment comprises:

- at least two chambers that are attached so as to rotate together when placed on a roller table. The two chambers can be formed from one bottle having a partition or two separate bottles. The size of each chamber may be varied. The bottle(s) may be constructed of any material such as glass, polyethylene, polycarbonate or polystyrene.
- an orifice or opening between the chambers to provide fluid correspondence between the two. The orifice may be a simple hole or may contain a valve or shut-off apparatus.
- a length of tubing arranged so as to form a spiroid pump, the tubing being placed around the inside surface of the chamber that serves as a medium reservoir. The tubing may be of any size according to the rate of delivery of medium desired, a tubing of larger diameter delivering more volume than tubing of smaller diameter. Likewise, the length of the tubing is not critical, although as least two spiral turns are required to give optimal delivery. The tubing can be made from any convenient material, such as silicone rubber, polyethylene, polycarbonate, and the like.

EXAMPLE 1

A Simple One-piece Model

Figure 1:
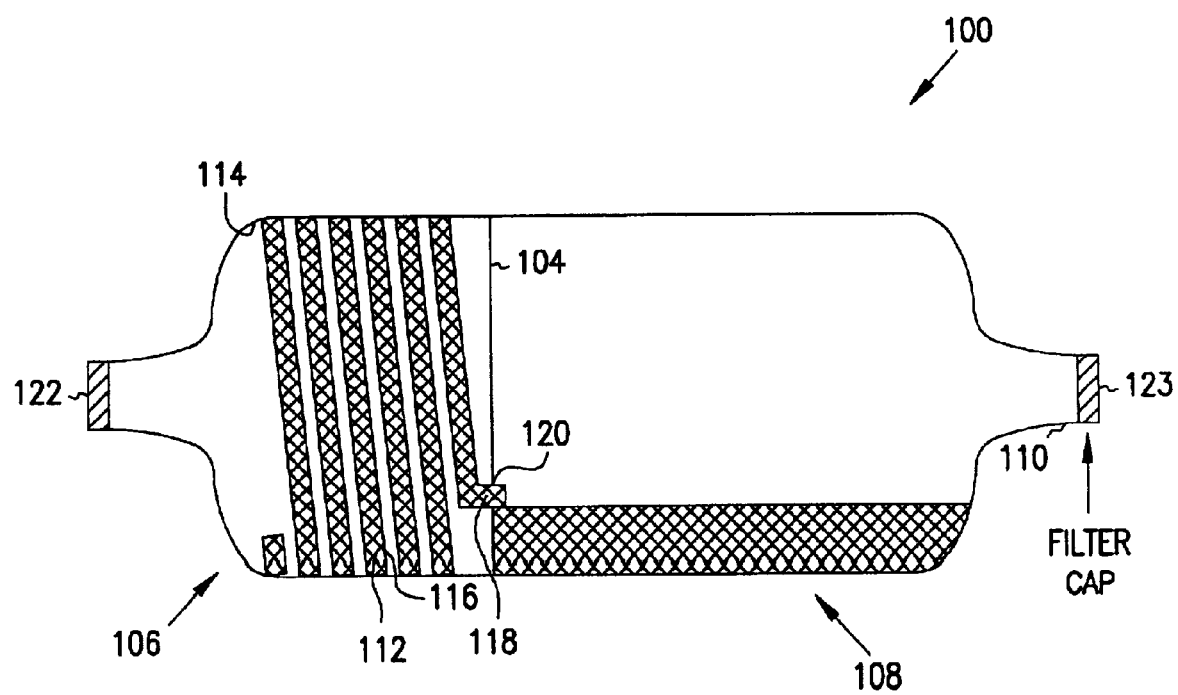
FIG. 1 shows a reservoir chamber formed by placing an impermeable partition to form a reservoir chamber and a growth chamber within one bottle.

The simple model consists of a two chamber glass roller bottle with a glass partition dividing the chambers. The growth chamber is 5.0 inches long, the fresh medium reservoir is 4.0 inches long and the diameter is 4.7 inches. The growth chamber holds a maximum of 300 milliliters of liquid before the liquid level will spill out over the lip of the bottle. Biopharmaceutical grade silicone tubing with a 0.0625 inch inner diameter and 0.125 inch outer diameter was coiled around the inside of the fresh medium reservoir. In this model, the tubing is placed inside larger diameter tubing (0.125 inch inner diameter, 0.0.375 inch outer diameter) to provide a more stable coil. The coiled tubing acts as a spiroidal pump while the bottle rotates on its horizontal axis. One end of the spiroid protrudes through a 0.125 inch opening in the partition and delivers fresh medium to the growth chamber. The volumetric feeding rate was determined by the rotation rate and the liquid level in the fresh medium reservoir through which the spiroid rotates and picks ups alternating "plugs" of liquid and gas. Both ends of the bottle had removable caps to allow access to the chamber. The caps were vented with a 0.2 micrometer filter. FIG. 1 is a diagram of this model.

EXAMPLE 2

Growth of Hybridoma Cells

Hybridoma cells were selected to test the growth in the roller bottle of example 1 (the "test" bottle.) Hybridoma cells are large and thus susceptible to mechanical stress leading to inhibition or breakage. It was proposed that if these more fragile cells could be grown in the test bottle, all other cells of interest could be grown successfully. The test bottle was inoculated with a culture of AE-1 hybridoma cells, which produce monoclonal antibodies against human acetylcholinesterase. Cultures were grown in PHM-II medium, a protein-free, serum-free hybridoma medium (life Technologies, Buffalo, N.Y.). The medium was supplemented with 0.2 percent fetal bovine growth serum and an antibiotic/antimycotic solution to prevent infection of the cultures.

Two types of tests were performed: the objective of the first was to test the bottle's ability to maintain a viable culture over a period of several days, and the objective of the second was to compare monoclonal antibody production in the test bottle to production in a conventional roller bottle. Fresh liquid medium was fed to the culture in the test bottle continuously via the rotating spiroid located in the fresh medium reservoir. The diameter of the tubing and the rotation of the rollers were adjusted so as to deliver 100 milliliters of fresh medium per day. An equivalent volume of fresh medium was added manually to the culture in the conventional bottle once each day. A volume of culture medium equal to the amount added each day to both cultures was removed each day from each culture. Cultures grew in batch mode for the first 48 hours; addition of fresh medium was initiated in both bottles at this time. Tests in both the test and conventional bottles were initiated when cell densities reached 200,000 cell/ml.

FIG. 2 shows the results of the test to determine the test bottle's ability to maintain a viable cell culture over a period of several days. The test was conducted with a 200 ml operating volume and a dilution rate of 50 percent, meaning 100 ml of fluid was added and removed each day. The figure shows both total and viable cell counts over a ten day period. As seen in the figure, steady-state viable cell density is 690,000 cells/ml and the steady-state total cell density is 770,000 cells/ml, a viability equal to a very acceptable 90%.

FIG. 3 shows results of the test to compare monoclonal antibody production in the test bottle to production in a conventional roller bottle. This test was conducted with a dilution rate equal to 37.7%. As calculated from data in the figure, steady-state antibody production is 41.2 µg/ml/day in the test and 40.3 µg/ml/day in the conventional roller bottle.

The test bottle, therefore, demonstrates the ability to maintain viable cultures with no loss of antibody production in an automated fashion, whereas the conventional roller bottles require manual, daily attention. Although medium was removed daily from both bottles, this was done by choice for a more accurate comparison between the two; cultures in the test bottle can be left unattended while still being fed fresh medium, while cultures in the conventional roller bottles require continuous manual attention in order to achieve the same results.

The steady-state cell density in the test bottle at this dilution rate was 600,000 cells/ml. Antibody production on a per cell basis, therefore, is 69 $\mu g/10^6$ cells/day versus 37 $\mu g/10^6$ cells/day in the conventional bottle. The reduced cell count may be a result of the increased antibody production: the cells are utilizing energy for antibody production rather than for cell division. These higher producing cells may be Selected for inoculation into new culture that may result in more efficient use of the costly culture medium.

EXAMPLE 3

Test Bottle With Overflow Chamber

The simple test bottle may be fitted with a third chamber to serve as an overflow catchment. This third chamber will have an opening similar in size to that of the culture chamber and will have a connection which is preferably fitted with a valve and connect-disconnect fitting.

Figure 4:
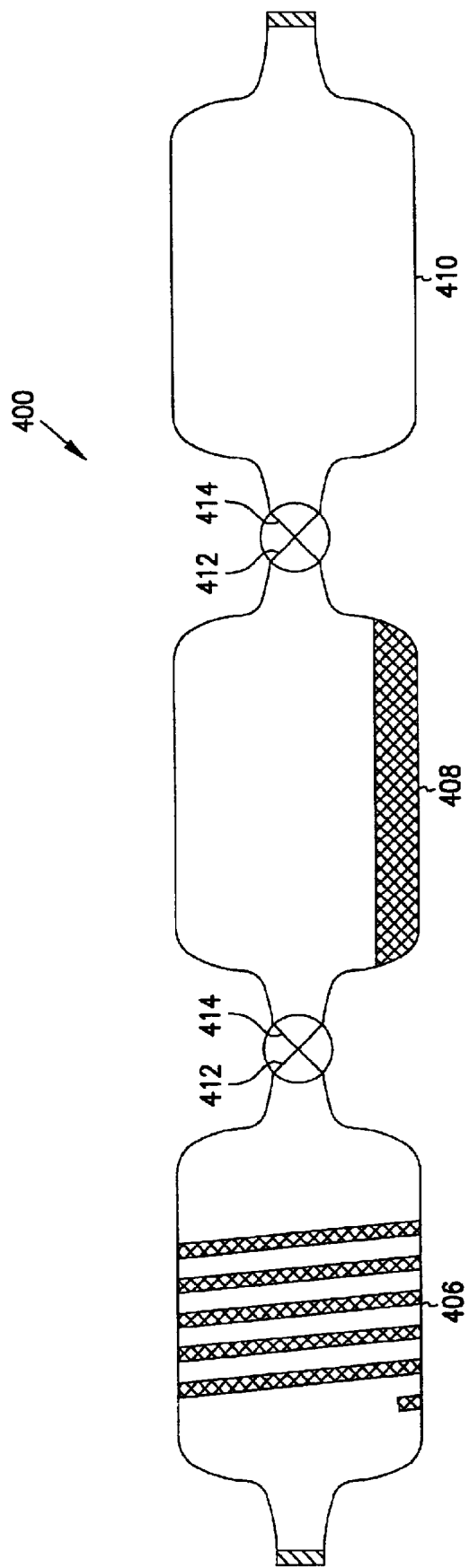
FIG. 4 shows a reservoir chamber attached to one end of the growth chamber and a collection bottle attached to the other end.

When the fluid in the growth chamber reaches a predetermined volume, such as 300 ml for the test bottle of example 1, the fluid will overflow into the third chamber. As desired, the valve can be closed and the bottle disconnected from the growth chamber, while an empty bottle is fitted in its place. The collected fluid can be treated to recover product. FIG. 4 illustrates a test bottle fitted with a catchment bottle. In this illustration, the reservoir bottle is separate and is likewise fitted with a valve and connect/disconnect fitting. Such a removable reservoir and catchment apparatus can be run indefinitely without opening the growth chamber. However, the one-piece test bottle can equally well be attached to the catchment bottle.

The invention has been described in terms of the foregoing embodiments, however, one skilled in the art can readily make variations and modifications in these embodiments. Such variations and modifications are considered to be within the scope and spirit of the following claims.

We claim:

1. An apparatus comprising a reservoir chamber and a tubular feed line spirally disposed on an inner surface of said reservoir chamber, said reservoir chamber being operably attached to a rotatable growth chamber, with an inlet of the tubing within the reservoir chamber and the outlet of the tubing within the growth chamber so that when the growth chamber is rotated the reservoir chamber rotates synchronously causing fluid to move from the reservoir chamber to the growth chamber and wherein the reservoir chamber and the growth are within one bottle and are separated by an impermeable partition.

2. A roller bottle comprising a reservoir chamber and a tubular feed line spirally disposed on an inner surface of said reservoir chamber, said reservoir chamber being operably attached to a rotatable growth chamber, with an inlet of the tubing within the reservoir chamber and the outlet of the tubing within the growth chamber so that when the growth chamber is rotated the reservoir chamber rotates synchronously causing fluid to move from the reservoir chamber to the growth chamber, wherein the reservoir chamber and growth chamber are separated by at least one impermeable partition.

* * * * *